United States Patent
Fischer et al.

(10) Patent No.: US 7,076,021 B2
(45) Date of Patent: Jul. 11, 2006

(54) APPARATUS FOR MEASUREMENT OF THE THICKNESS OF THIN LAYERS

(75) Inventors: Helmut Fischer, Sindelfingen (DE); Volker Rössiger, Sindelfingen (DE)

(73) Assignee: Immobiliengesellschaft Helmut Fischer GmbH & Co. KG, Sindelfingen (DE)

( * ) Notice: Subject to any disclaimer, the term of this patent is extended or adjusted under 35 U.S.C. 154(b) by 0 days.

(21) Appl. No.: 10/739,673

(22) Filed: Dec. 17, 2003

(65) Prior Publication Data

US 2004/0131148 A1 Jul. 8, 2004

(30) Foreign Application Priority Data

Dec. 18, 2002 (DE) ................. 102 59 696

(51) Int. Cl.
*G01N 23/223* (2006.01)

(52) U.S. Cl. .......................... 378/50; 378/54

(58) Field of Classification Search ............ 378/50, 378/54, 89
See application file for complete search history.

(56) References Cited

U.S. PATENT DOCUMENTS

| | | | | | |
|---|---|---|---|---|---|
| 4,475,041 A | * | 10/1984 | Fischer | .................. | 250/358.1 |
| 4,597,093 A | * | 6/1986 | Fischer | .................. | 378/50 |
| 5,299,252 A | * | 3/1994 | Takahashi | .................. | 378/50 |

* cited by examiner

*Primary Examiner*—Edward J. Glick
*Assistant Examiner*—Jurie Yun

(57) ABSTRACT

An apparatus for measurement of the thickness of thin layers by means of X-rays using an X-ray tube which emits X-rays which are directed at a layer to be measured, has at least one aperture apparatus arranged between the X-ray tube and the layer to be measured. The apparatus includes an area absorbing X-rays and an aperture opening. At least one aperture opening in the aperture apparatus has a geometric shape which, seen in the beam direction, projects an area which at least in places is matched to the geometry of the layer to be measured.

14 Claims, 4 Drawing Sheets

APPARATUS FOR MEASUREMENT OF THE THICKNESS OF THIN LAYERS

CROSS-REFERENCES TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The invention relates to an apparatus for measurement of the thickness of thin layers by means of X-ray radiation.

2. Relevant Art

An apparatus of this generic type is known from DE 32 39 379 C2, which is used for measurement of the thickness of thin layers on the basis of the X-ray fluorescence principle. This apparatus has an X-ray tube which emits X-rays which are directed at a layer to be measured on a measurement object. An aperture apparatus is provided between the measurement object of [sic] the X-ray tube at a variable distance from the measurement object or from the layer to be measured, and limits the X-ray radiation to a measurement point on the layer to be measured. The florescence rays which are emitted from the irradiated measurement object are detected and evaluated by a detector. A semi-reflective deflection mirror is provided in the beam path between the aperture apparatus and the X-ray tube, allows the X-ray radiation to pass through, and allows a view of the measurement object and of the layer to be measured.

The aperture apparatus of this apparatus has two or more through-holes which are arranged at a fixed distance from one another and have different sizes. These through-holes can be chosen as appropriate for the measurement task, as a result of which it is possible to detect small measurement points or zones which can be defined exactly. This apparatus allows individual very small areas on the layer to be measured to be determined exactly. A high intensity is required for this purpose, and this acts on the measurement object. The longer the measurement time, the greater is the measurement precision which can be detected.

The measurement of the thickness of thin layers can also be carried out for mass-produced items. For example, in the case of valve parts for injection pumps, it is necessary to detect a layer thickness which has been applied by an electrochemical plating process. Millions of these parts are produced. The measurement process for determining the thickness of thin layers must take only a short measurement time.

SUMMARY OF THE INVENTION

The invention is therefore based on the object of developing the apparatus of this generic type so as to allow the thickness of thin layers to be measured exactly within a very short measurement time.

This object is achieved by an apparatus for measurement of the thickness of thin layers by means of X-rays using an X-ray tube which emits X-rays which are directed at a layer to be measured, comprising at least one aperture apparatus arranged between the X-ray tube and the layer to be measured, which comprises an area absorbing X-rays and has an aperture opening, wherein at least one aperture opening in the at least one aperture apparatus has a geometric shape which, seen in the beam direction, projects an area which at least in places is matched to a geometry of the layer to be measured. Further refinements and developments are specified in the other claims.

The short measurement time for mass-produced items, in which the thickness of the coating is intended to be detected, is achieved by providing an aperture apparatus which has an aperture opening with a geometric shape which, seen in the beam direction, projects an area which at least in places is matched to the geometry of the layer to be measured. This allows the surface of the layer to be measured to be irradiated uniformly, so that the entire measurement surface can be recorded within just one measurement process. This at least partial matching of the aperture opening according to the geometry of the layer to be measured allows the measurement time to be shortened for mass-produced items. This is of considerable financial importance. Shortening the measurement time allows a higher item throughput rate. This allows 100% testing to be carried out, and the costs for quality testing to be reduced. This refinement of the aperture apparatus according to the invention allows X-rays to be used for non-contacting measurement of mass-produced items, for which only a very short measurement time is available.

One refinement of the invention provides for the aperture opening of the aperture apparatus to have an absorbent area which surrounds one aperture opening, and at least one absorbent area to be provided within the aperture opening or at least partially adjacent to it. This refinement allows the X-rays to be matched to a large number of geometries, and to be projected onto the measurement surface. The arrangement of at least one absorbent area within the aperture opening allows sub-areas in the projection of the beams onto the surface to be masked out on the layer to be measured. This allows beam guidance which is matched to the measurement object or to the surface of the layer to be measured.

The at least one through-opening which is provided within the aperture opening has, according to one preferred embodiment, a gap width and/or a gap length which, in the beam direction, projects an area onto the surface of the layer to be measured, which is of the same size as or is smaller than the area of the layer to be measured. The aperture apparatus can thus be used to illuminate the entire surface of the layer to be measured, within one measurement process. The optional geometric configuration of the length and width of the at least one through-opening allows those areas which are relevant for quality testing to be measured at the same time, and allows the other areas to be masked out. The aperture apparatus can thus be matched to a specific measurement task.

The aperture apparatus has at least one through-opening, in the form of a gap, between the at least one aperture opening and the absorbent area within it or adjacent to it. This allows filigree structures and line forms or areas to be formed, through which the radiation passes and strikes the surface of the layer to be measured. This refinement of the at least one through-opening in the form of a gap allows even areas which are coated in a highly filigree manner as well as areas whose surface extent is variable to be measured.

At least one through-opening which forms an annular gap is preferably provided. This allows a so-called ring aperture or ring collimator to be provided which is used in particular for measurement of the layers on rotationally symmetrical parts. These rotationally symmetrical parts may have one or more circular or annular areas to which a coating is applied and whose layer thickness is to be tested.

In one embodiment, at least one web is provided between the at least one through-opening, which is in the form of a gap and is arranged with respect to an annular gap, and this web positions the absorbent area which is arranged within the aperture opening. The web or webs is or are advantageously designed to be very narrow thus resulting in virtually uniform illumination or irradiation of the surface of the layer to be measured, depending on the adjacent through-openings.

Alternatively, it is possible to provide for a large number of webs, composed of thin wire by way of example, to be provided, spaced apart from one another. The wire or wires can be provided on one side of the aperture apparatus or as a layer within the aperture apparatus.

According to a further refinement of the invention, the absorbent area or areas which is or are arranged within the aperture opening can be arranged outside the plane of the aperture opening. For example, a reduction in the gap width of the through-openings can be achieved by moving the inner absorbent area or areas in the direction of the beam source. This allows the projected area of the radiation in the measurement plane to be reduced.

This makes it possible, for example, to choose a thinner material for the aperture apparatus, which in turn can be processed easily. The aperture apparatus is preferably formed from organic or inorganic glass, which is preferably transparent. The use of a lead glass is particularly appropriate. Depending on the required energy composition of the radiation, the thickness of the lead glass can be reduced in order nevertheless to achieved absorption of the X-ray radiation. Since a large area is irradiated for the measurement, a lower radiation intensity may be sufficient to carry out the measurement.

The through-openings in the aperture opening are preferably formed at right angles to the surface of the aperture apparatus. These through-openings may likewise at least slightly widen, seen in the beam direction.

A further embodiment of the invention provides for the aperture apparatus to be designed such that it can rotate. The deflection from a horizontal arrangement or from a parallel arrangement to the measurement plane allows, for example, a through-opening which projects an elliptical area to be provided using an aperture apparatus with an annular gap. One aperture apparatus can therefore be matched to a number of geometric shapes of the surface of the object to be measured.

In a further alternative embodiment of the invention, it is possible for at least one area within the aperture opening or at least partially adjacent to it to be arranged such that it can rotate with respect to the aperture opening. In the case of a ring aperture, by way of example, the inner absorbent area can be arranged such that it can rotate to allow the creation of an aperture apparatus whose transmission can be varied.

BRIEF DESCRIPTION OF THE FIGURES

The invention as well as further embodiments and developments of it will be described and explained in more detail in the following text with reference to the example which is illustrated in the drawing. The features which can be found in the description and in the drawing may be used, according to the invention, individually in their own right or in any desired combination together. In the figures.

DETAILED DESCRIPTION OF THE INVENTION

Figure 1:
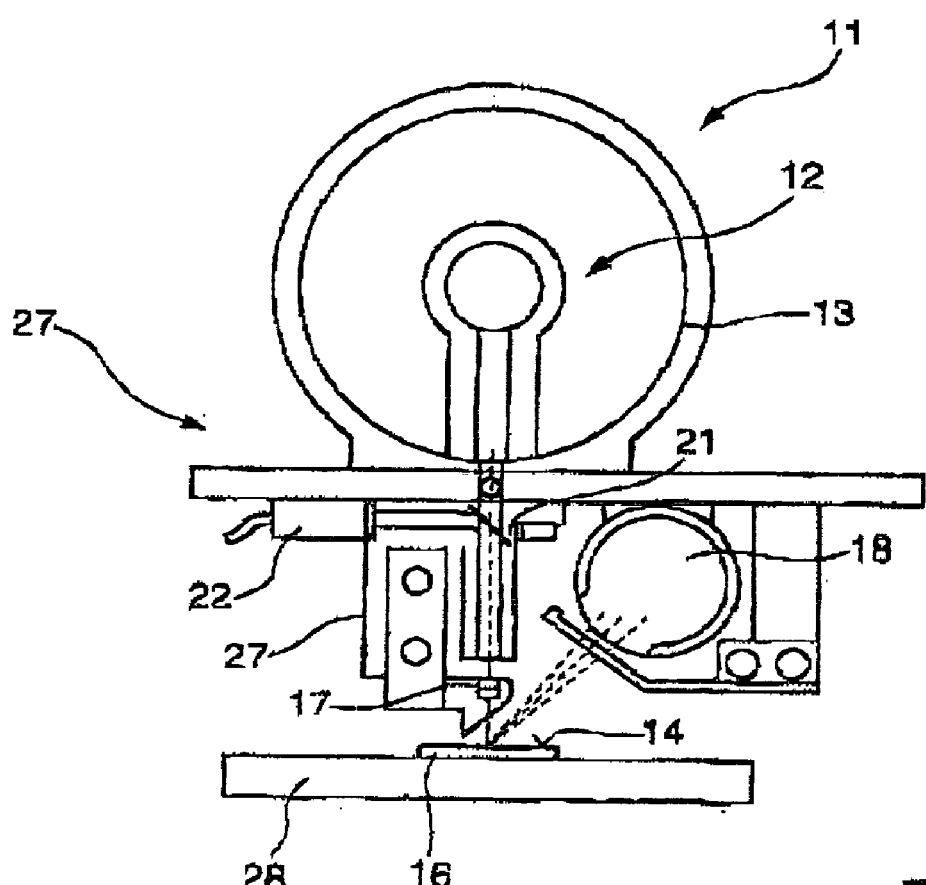
FIG. 1 shows a schematic view of an apparatus for measurement of thin layers by means of X-ray radiation.

FIG. 1 shows an apparatus 11 for measurement of the thickness of thin layers by means of X-ray radiation, in particular by means of X-ray fluorescence radiation. This apparatus 11 has an X-ray tube 12 for producing X-rays in a housing 13. X-rays emerge through an opening in the housing 13 and strike a surface 14 of a measurement object 16. A specific surface area of the X-rays is projected onto the surface 14 of the measurement object 16 by means of an aperture apparatus 17 which is arranged at a defined distance from the surface 14 of the measurement object 16. A proportional target tube 18 or a detector detects the florescence radiation or secondary radiation emitted by the measurement object, and evaluates this radiation with the assistance of a data processing system.

The apparatus 11 has a semi-reflective mirror 21 which is arranged in the beam path of the X-rays and allows the image of the surface 14 of the measurement object 16 to be seen via optics, to be recorded by means of an electronic indicator 22, and to be output via a monitor.

Figure 2:
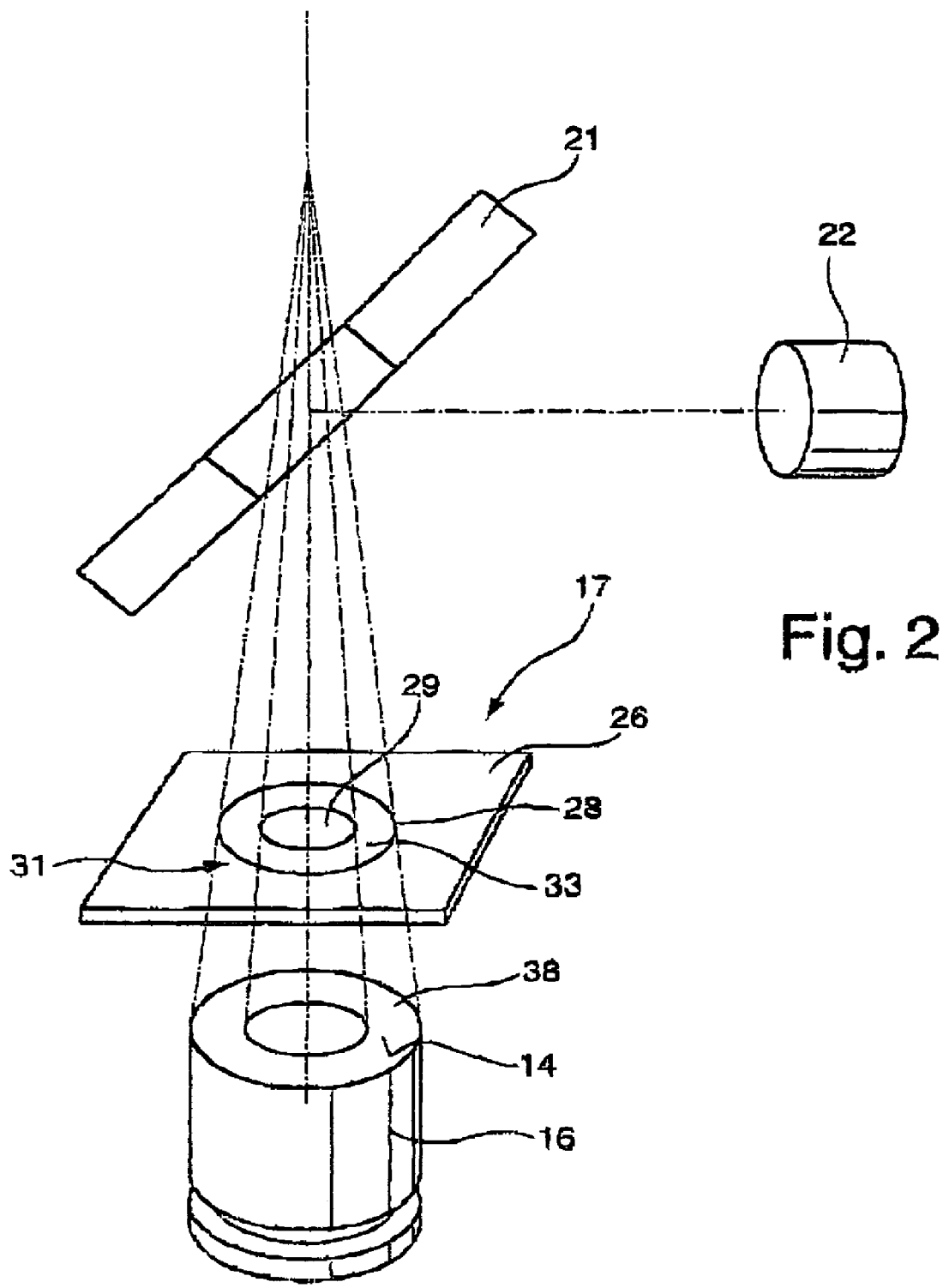
FIG. 2 shows a schematic view of a beam path with an aperture apparatus according to the invention.

FIG. 2 shows the beam path from the X-ray tube to the measurement object 16 in perspective form and enlarged, not to scale. The aperture apparatus 17 has an absorbent area 26 which, for example, is clamped into an adjusting mechanism 27, via which the distance to the surface 14 of the measurement object 16 can be adjusted. The aperture apparatus 17 has an aperture opening 28 which is adjacent to the outer absorbent area 26. An inner absorbent area 29 is arranged within the aperture opening 28, through which an annular gap 31 is formed for the aperture opening 28. The inner absorbent area 29 is positioned with respect to the aperture opening 28 by means of webs 32, which are illustrated in more detail in the plan view shown in FIG. 3. The formation of an annular gap 31 which, according to the exemplary embodiment, is formed from three through-openings 33, makes it possible for the X-rays to project an annular area 36 onto the surface 14 of the measurement object 16. This annular area 36 corresponds to a measurement area, and its layer thickness on the measurement object is determined by this apparatus 11.

According to the exemplary embodiment, the measurement object 16 is a rotationally symmetrical component which is used in an injection pump in motor vehicles. A coating 38 is applied to an end surface 37 and at least in places extends to the side edges during the electrochemical plating process that is preferably used. This coating 38 is, for example, a chromium coating, whose layer thickness is to be measured.

These measurement objects 16 which are illustrated by way of example are mass-produced items, for which 100% testing must be carried out. The object in this case is to test the layer thickness of the end surface 37, and to ensure that the applied coating 38 has at least the required layer thickness.

Figure 3:
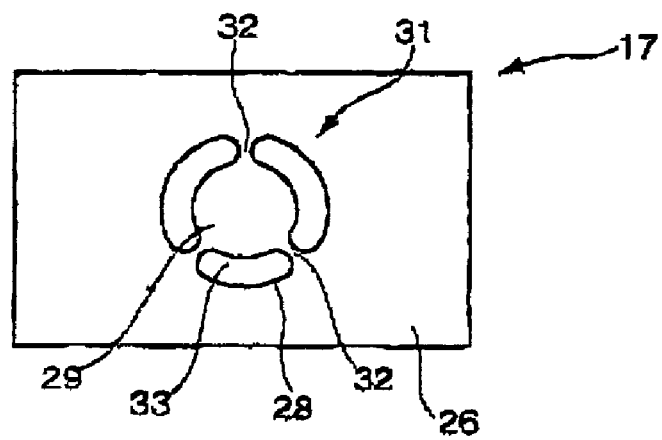
FIG. 3 shows a schematic plan view of the aperture apparatus shown in FIG. 2, FIGS. 4a and b show a schematic section illustration of a measurement object in different measurement positions during a layer thickness measurement, FIGS. 5a and b show a schematic illustration of an alternative embodiment of an aperture apparatus.

The refinement of the aperture apparatus 17 as shown in FIGS. 2 and 3, which is also referred to as a ring collimator, makes it possible for the layer thickness of the annular area 36 to be recorded within a measurement time of a few seconds, for example one second. The aperture apparatus 17 allows the X-rays to arrive at the surface 14 uniformly. The webs 32 which are arranged in between are designed to be comparatively thin, so that their shadow is negligible.

Figure 4A:
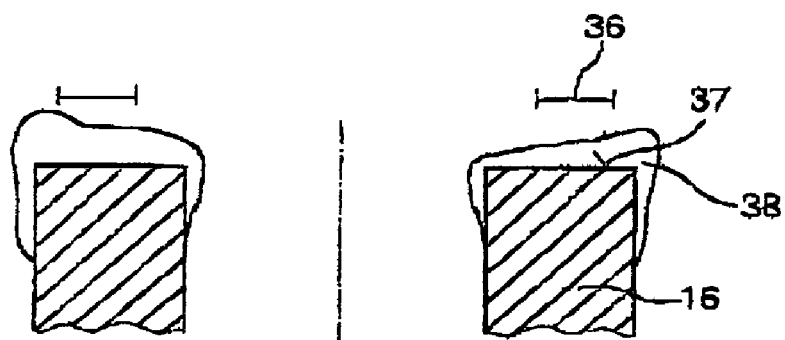

FIG. 4a shows a schematic section illustration of the measurement object 16. When the measurement object 16 is in an ideally aligned position with respect to the beam path, an annular area 36 is projected onto the coating 38 on the end surface 37, as is shown in FIG. 4a. This annular area 36 is preferably positioned in the central area.

These components have the particular feature that the coating 38 increases from the inside to the outside. The annular area 36 is provided matched to this such that this has the tendency to be more adjacent to the outer edge area than to the inner edge area of the circumferential surface. The width of the annular area 36 is matched to the width of the measurement area or to the end face 37 of the measurement object 36. The determined data is integrated by means of an evaluation unit from the emitted secondary radiation from the annular area, in order to determine the layer thickness.

Figure 4B:
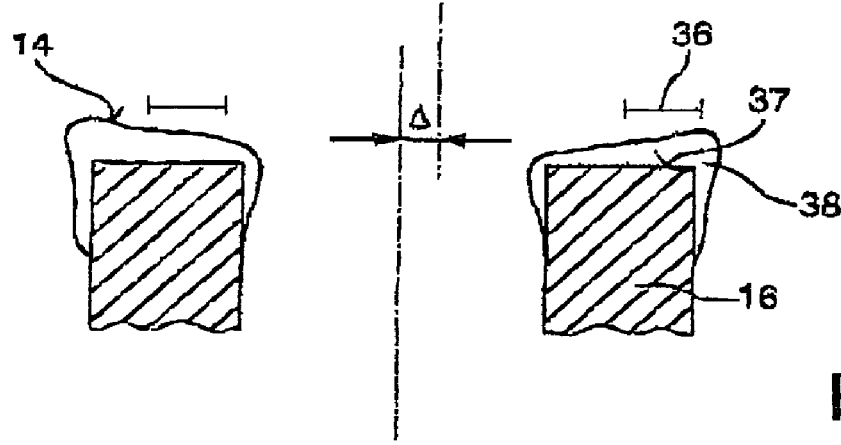

This ring aperture apparatus has the advantage that it is insensitive to tolerances. By way of example, FIG. 4b shows the measurement object 16 positioned with a lateral offset with respect to the beam axis. As can be seen from the positioning of the annular area 36 with respect to the coating 38, a section with thicker coating is irradiated on the right-hand side than on the left-hand side. The determination of an integral value over the entire annular area results in averaging, with a more valid value thus being obtained.

This complete, or essentially complete, irradiation of the annular area allows 100% testing of mass-produced items to be carried out in a short time. This is particularly advantageous in the case of sensitive surfaces. The larger measurement area which is provided by the aperture apparatus in comparison to a conventional spot measurement results in more primary radiation and thus more emitted secondary irradiation being available that a detector can record. A shorter measurement time can thus be achieved. In the case of the measurement object which is described in the exemplary embodiment, measurement times of, for example, one second or less can be achieved. This allows a non-contacting measurement to be carried out using X-ray florescence even for short cycle times.

In principle, the configuration of the aperture apparatus 17 can be varied in many ways and can be matched to the respective geometry of the surface 14 of the measurement object 16 or of the surface areas of a measurement object 16. By way of example, the annular area 36 may extend over the entire wall thickness of a rotationally symmetrical component as is illustrated in FIGS. 4a and b. The ring width of the annular area 36 is optionally adjustable. The shape and contour of individual ring segments can likewise be varied. By way of example, the webs 32 may cover a considerably greater proportion of the annular area. Furthermore, instead of one or more webs, for example as shown in FIG. 3, which are composed of the same material as the absorbent areas wires, for example, can be provided which position the inner area 29 with respect to the outer area 26. By way of example, wires or a wire mesh can be cast in an aperture apparatus 17 formed from lead glass.

Furthermore, alternatively, it is possible to provide for the inner absorbent area 29 which is illustrated, by way of example, in the form of a circular disc to be held by means of a shaft which can rotate. This allows variable transmission to be achieved, as a function of the desired measurement area, by rotation of the inner absorbent area 29. The inner absorbent area 29 may have a closed position, in which the aperture opening 28 is closed. By way of example, two sickle-shaped areas can be released by slightly opening the aperture opening 28 through a few angular degrees, to project corresponding areas onto the surface 14 of the measurement object 16. Virtually complete irradiation can likewise be made possible by rotation through 90°.

The aperture apparatus 17 is formed from organic or inorganic glass. Transparent lead glass is preferably used, in order to look at the measurement object through an indicator 22. The glass thickness which is used to achieve the absorption of the X-ray radiation is dependent on the beam quality of the X-ray radiation. For example, lead glass with a wall thickness of less than 8 mm, and preferably 1 to 4 mm, may be used. The aperture apparatus 17 may have treated upper and lower faces. Coatings such as metal may likewise be provided.

The aperture opening 28 may have any desired geometry and shape in the area 26, and the inner absorbent area 29 may also be arranged in any desired way with respect to the opening 28. Any geometric structures of measurement objects 16 which have a coating and whose thickness has to be measured can be provided. For example, U-shaped or V-shaped through-openings may be formed. Clover leaf structures, or a number of annular structures arranged in a circle with respect to one another may likewise be formed. The width and length of the through-openings 33 as well as the number and the size thereof and number of the inner absorbent areas 29 is variable and can be combined in a large number of ways.

By way of example, the aperture apparatus 17, which is illustrated as a ring collimator, can image an elliptical annular area 36 by rotation about a horizontal axis. This tilting about a rotating axis may have tilting about at least one further rotation axis superimposed on it.

Figure 5A:
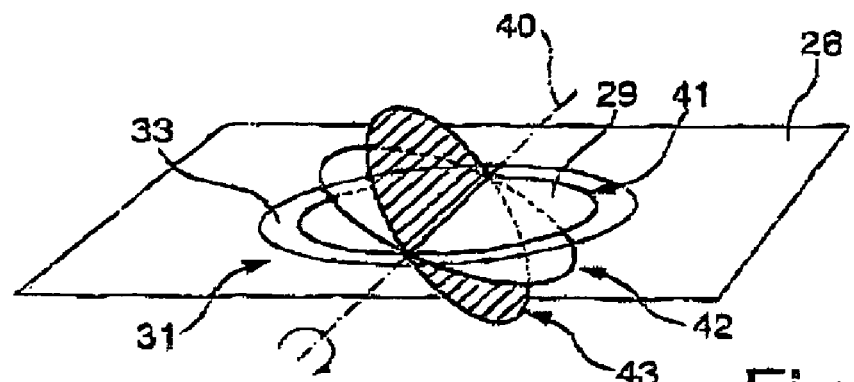

FIGS. 5a and b show a further alternative embodiment of an aperture apparatus 17. In this refinement, the inner absorbent area 29 is formed by a flap which can rotate and which is arranged such that it can rotate about an axis 40 out of the plane. This axis may be connected to a drive unit, thus making it possible to set a variable position for the inner absorbent area 29. This drive unit may allow very fine adjustment of an angular position.

By way of example, as is shown by position 41, the inner absorbent area 29 is provided in the same plane as the outer area 26. In this arrangement, a projected area is produced which, as shown in FIG. 5b, is represented by the number 41'.

Figure 5B:
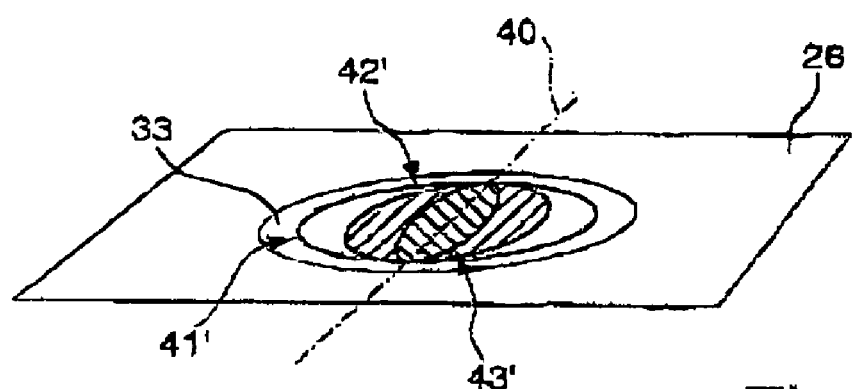

In this exemplary embodiment, an annular opening 33 is provided, which is also imaged as an annular area 33 in FIG. 5b. Alternatively, it is possible to provide for the inner area 29 to rest flush against the outer area 26 in a position 41, thus effectively resulting in there being no path for the X-ray radiation.

If the axis is rotated through a few angular degrees, the inner area 29 is moved, for example, to a position 42. This results in a projected area 42' being covered and, apart from this, in the beams striking the measurement surface.

A further position 43 which is illustrated by way of example forms an even smaller area 43', so that the area of the incident radiation becomes larger. At a maximum of 90°, the rotation of the inner area 29 can shadow a minimal area, which is negligible. The preferable use of a step-by-step adjustment process allows various positions to be moved. The illustrated geometry of the inner area 29 or of the flap which can rotate is shown only by way of example, and is not restricted to this.

Figure 6:
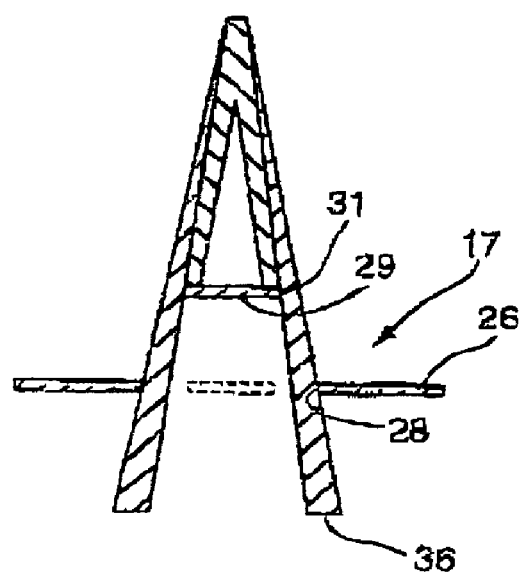
FIG. 6 shows a schematic illustration of a beam path with an alternative embodiment of an aperture apparatus to that shown in FIG. 2.

FIG. 6 shows a further alternative refinement of an aperture apparatus 17. This refinement provides for the inner absorbent area 29 to be moved out of the plane of the outer area 26 and, for example, to be arranged offset in the direction of the beam source, although it can likewise be moved in the opposite direction. This allows the gap width to be varied while maintaining the basic geometry of the through-openings 33. In addition, both the area 26 and the area 29 can be arranged such that they can be adjusted independently of one another about at least one rotation axis. The inner area 29 may be provided separately from the area 26 and is held there using wires or further suitable means in order to allow it to be arranged separately from the outer area 26.

It is self-evident that triangular, square, polygonal, elliptical or other open circular shapes or wavy line shapes or the like can be provided instead of an annular gap, in particular with geometries of the surface of a layer to be measured being provided for which a portion of the surface of the measurement object is masked out from the X-ray radiation or from the area which is projected onto the surface of the measurement object.

We claim:

1. Apparatus for measurement of the thickness of thin layers by means of X-rays using an X-ray tube (12) which emits X-rays which are directed at a layer to be measured, comprising having at least one aperture apparatus (17) arranged between the X-ray tube (12) and the layer to be measured, wherein the at least one aperture apparatus comprises an area (26) absorbing X-rays and has at least one aperture opening (28), wherein said at least one aperture opening (28) wherein the absorbent area (26) surrounds said at least one aperture opening (28), and in the at least one aperture apparatus (17) has a geometric shape which, seen in the beam direction, projects an area which at least in places is matched to the geometry of the layer to be measured, and wherein at least one inner absorbent area (29) is provided within said at least one aperture opening (28) or is at least partially adjacent to said at least one aperture opening (28), by means of which at least one through-opening (33) is formed in said at least one aperture opening (28).

2. Apparatus according to claim 1, wherein the at least one through-opening (33) has a length and a width which, in the beam direction, projects an area onto the layer to be measured which is of the same size as or is smaller than the geometry of the layer to be measured.

3. Apparatus according to claim 1, wherein one of the at least one through-opening (33) comprises a gap formed between the at least one aperture opening (28) and the inner absorbent area (29).

4. Apparatus according to claim 3, wherein the at least one through-opening (33) comprises an annular gap.

5. Apparatus according to claim 3, wherein the at least one through-opening (33), comprises an annular gap which is interrupted by at least one web (32).

6. Apparatus according to claim 5, wherein a substantial number of webs (32) are provided and are spaced apart from one another.

7. Apparatus according to claim 3, wherein the at least one through-opening (33) is comprised of right angles to a surface of the aperture apparatus (17).

8. Apparatus according to claim 1, wherein said inner absorbent area (29) within said at least one aperture opening (28) or at least partially adjacent to said at least one aperture opening is positioned in a plane outside the at least one aperture opening (28).

9. Apparatus according to claim 1, wherein the aperture apparatus (17) comprises organic or inorganic glass.

10. Apparatus according to claim 9, wherein the aperture apparatus (17) comprises transparent glass.

11. Apparatus according to claim 9, wherein the aperture apparatus (17) comprises lead glass.

12. Apparatus according to claim 1, wherein the aperture apparatus (17) is arranged to pivot about at least one axis.

13. Apparatus according to claim 1, wherein the area which is projected by the aperture apparatus (17) onto the layer to be measured with X-rays emits secondary radiation, from which secondary radiation an integral value is determined with regard to the thickness of the layer.

14. Apparatus for measurement of the thickness of thin layers by means of X-rays using an X-ray tube (12) which emits X-rays which are directed at a layer to be measured, comprising having at least one aperture apparatus (17) arranged between the X-ray tube (12) and the layer to be measured, which comprises an area (26) absorbing X-rays and has at least one aperture opening (28), wherein the at least one aperture opening (28) in the at least one aperture apparatus (17) has a geometric shape which, seen in the beam direction, projects an area which at least in places is matched to the geometry of the layer to be measured, and further comprising at least one absorbent area (29) is arranged in the at least one aperture opening (28) and which is pivotably mounted.

* * * * *